US00PP28996P2

(12) United States Plant Patent
Bradford et al.

(10) Patent No.: US PP28,996 P2
(45) Date of Patent: Feb. 27, 2018

(54) PEACH TREE NAMED 'JULY PRINCESS'

(50) Latin Name: *Prunus persica*
Varietal Denomination: JULY PRINCESS

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/530,228

(22) Filed: Dec. 15, 2016

(51) Int. Cl.
*A01H 5/08* (2006.01)

(52) U.S. Cl.
USPC ..... Plt./198

(58) Field of Classification Search
USPC ..... Plt./198
See application file for complete search history.

(56) References Cited

U.S. PATENT DOCUMENTS

PP12,570 P2 4/2002 Bradford
PP24,729 P3 8/2014 Bradford

*Primary Examiner* — Annette H Para

(57) ABSTRACT

The present invention relates to a new and distinct variety of peach tree, *Prunus persica*, broadly characterized by a large size, vigorous, hardy, self-fertile, productive and regular bearing tree. The variety blooms during the early to mid blooming season and requires about 500 chilling hours. The fruit matures under the ecological conditions, described in early to mid July with the first picking on Jul. 3, 2016. The fruit is uniform, medium in size, fairly globose in shape, freestone in type, firm in texture, yellow in flesh color, mostly red in skin color, and moderately acidic in flavor.

1 Drawing Sheet

Botanical classification: *Prunus persica.*
Variety denomination: 'JULY PRINCESS'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'JULY PRINCESS'.

The present variety was hybridized by us in 2000 as a first generation cross using "43P318" (unpatented) peach as the selected seed parent and 'Snow Princess'(U.S. Plant Pat. No. 12,570) peach as the selected pollen parent. Upon reaching maturity the fruit from this cross was harvested, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2006 we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, '43P318' peach (unpatented), by having a vigorous tree, by being self-fertile, and by producing peaches that are freestone in type, mostly red in skin color, and yellow in flesh color, but is quite distinguished therefrom by blooming much earlier, by requiring much less chilling, and by producing peaches that mature about thirty days earlier.

The present variety is similar to its pollen parent, 'Snow Princess' peach (U.S. Plant Pat. No. 12,570), by having a vigorous tree with large blossoms, by being self-fertile, and by producing freestone peaches that are mostly red to pink in skin color, globose in shape, and firm in texture, but is distinguished therefrom by producing fruit that is acidic instead of sub-acidic in flavor, that is yellow instead of white in flesh color, and that matures about twelve days earlier.

The present variety is most similar to 'Red Princess' peach (U.S. Plant Pat. No. 24,729) by having large blossoms, by being self-fertile, and by producing peaches that are mostly red in skin color, yellow in flesh color, fairly globose in shape, lightly acidic in flavor, and firm in texture, but is distinguished therefrom by requiring less chilling hours, and by producing fruit that is freestone instead of clingstone in type, that is somewhat smaller in size, that has a bitter instead of sweet kernel, and that ripens about eighteen days later.

SUMMARY OF VARIETY

In summary, the present peach variety is characterized by a large size, vigorous, hardy, self-fertile, productive and regular bearing tree. The variety blooms during the early to mid blooming season and requires about 500 chilling hours. The fruit matures under the ecological conditions described in early to mid July with the first picking on Jul. 3, 2016. The fruit is uniform, medium in size, globose in shape, freestone in type, firm in texture, yellow in flesh color, mostly red in skin color, and moderately acidic in flavor.

DRAWING

The accompanying photograph consists of four whole fruits positioned to display the characteristics of the skin color and form, one divided fruit to reveal the flesh and stone, a tip shoot of new leaf growth, typical leaves, and three insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 7, 2016, on the original tree its sixteenth growing season. The blossom and flower descriptions were made the previous blooming season. All major color code designations are by reference to the Inter-Society Color Council, National Bureau of Standards. Common color names are also used occasionally.

It is to be noted that the 2016 fruit season in California was very warm during the spring and the ripening times of almost all varieties were about two weeks earlier than other years.

PARENTAGE

Seed parent: '43P318' (unpatented) peach.

Pollen parent: 'Snow Princess' (U.S. Plant Pat. No. 12,570) peach.

TREE

Size: Large, reaching and maintaining a height of 12' [3.66 m.] and a spread of 9' [2.74 m.] after sixteen growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 500 hours.

Trunk:

*Size*.—Medium, reaching a maximum diameter of 6¾" [171 mm.] after the sixteenth growing season.

*Texture*.—Medium, shaggy.

*Bark color*.—A Moderate yellowish brown [77. m.yBr] and Dark grayish brown [62. d.gy.Br] variegation with Light brown [57. l.Br] crevices present.

*Lenticels*.—Approximate Number Per Square Inch: 8. Color: Brownish gray [64. brGy]. Average Size: ⅛" [3.2 mm.] in length. The width is typically one fourth as much as the length. Shape: Eye-shaped.

Branches:

*Size*.—Medium, diameter of main scaffold is 2½" [63.5 mm.] measured 12" above the crotch, diameter of limb is 1¾" [44.5 mm.] measured 12" above the first fork.

*Texture*.—Fairly smooth on first and second year wood, increasing roughness with age.

*Color*.—1st Year Wood Topside: Grayish red [19. gy.R]. 1st Year Wood Underside: Brilliant yellow green [116. brill.YG]. Older Wood: A Light brown [57. l.Br] and Grayish brown [61. gy.Br] variegation.

*Lenticels*.—Number Per Square Inch: About 60 on second year wood. Color: Light yellowish brown [76. l.yBr]. Average Size: Medium, 1/16" [1.6 mm.] in length. The width is typically one fourth as much as the length. Shape: Eye-shaped.

Leaves:

*Size*.—Large. Average Length: 5¾" [146 mm.]. Average Width: 1⅞" [47.6 mm.].

*Arrangement*.—Alternate.

*Thickness*.—Medium.

*Form*.—Elliptical.

*Apex*.—Acuminate.

*Base*.—Acute, average angle of 75 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Light yellow green [119. l.YG].

*Petiole*.—Average Length: ½" [12.7 mm.]. Average Thickness: ⅛" [3.2 mm.]. Color: Moderate yellow green [120. m.YG].

*Stipules*.—Number: Usually 2 per leaf, up to 6 per growing tip. Average Length: ⅜" [9.5 mm.]. Color: Light yellow green [119. l.YG] becoming Very deep red [14. v.deep R] with age.

*Glands*.—Number: 2 to 4 per leaf. Position: Mostly alternate positioned near the intersection of petiole and base of blade. Form: Appear to be globose when young but take on a reniform shape with age. Size: Medium, about 1/48" [0.5 mm.] in diameter. Color: Brilliant yellow green [116. brill.YG] acquiring a Dark grayish red [20. d.gy.R] center with age.

*Leaf buds*.—Pointed, medium in size.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Free, not touching.

*Surface*.—Pubescent.

*Tip color*.—Light pink [4. l.Pk].

Flowers: Perfect, complete, perigynous, usually a single pistil, about thirty stamens, five sepal and petal locations alternately positioned.

*Type*.—Showy, large.

*Average flower diameter*.—2" [50.8 mm.].

*Average flower depth.*—7/16" [11.1 mm.] when fully open.
*Number of petals.*—Usually five, extra petal fragments occur occasionally, double blossoms rarely observed.
*Petal arrangement.*—Overlapping.
*Petal shape.*—Circular to oval.
*Petal margin.*—Entire, wavy.
*Average petal diameter.*—5/8" [15.9 mm.].
*Average petal length.*—11/16" [17.5 mm.].
*Petal apex.*—Rounded.
*Petal base.*—Rounded to somewhat truncate.
*Petal color.*—Light pink [4. l.Pk] toward the apex, Strong pink [2. s.Pk] toward the base on both sides.
*Anther color.*—Moderate red [15. m.R] over a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located about even with the nearby anthers.
*Stamen position.*—Typically located about 1/32" [0.8 mm] below the petals.
*Average pistil length.*—5/8" [15.9 mm.].
*Average stamen length.*—5/8" [15.9 mm.].
*Ovary.*—Pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—1/4" [6.4 mm.].
*Sepal width.*—3/16" [4.8 mm.].
*Sepal apex.*—Rounded to elliptical to match the sepal length and width.
*Sepal margin.*—Fairly smooth.
*Fragrance.*—Moderate.
*Blooming period.*—Medium to early, four days before 'Red Princess' (U.S. Plant Pat. No. 24,729) peach.
*Onset of bloom.*—One percent on Feb. 14, 2016.
*Date of full bloom.*—Feb. 22, 2016.
*Duration of bloom.*—One to two weeks, dependent on ambient temperature.
*Bloom density.*—Medium to heavy.
*Number per cluster.*—1 to 3 with single flowers most common.

FRUIT

Maturity when described: Firm ripe, Jul. 7, 2016.
Date of first picking: Jul. 3, 2016.
Date of last picking: Jul. 13, 2016.
Size: Mostly uniform, medium.
*Average diameter axially.*—2 7/8" [73 mm.].
*Average diameter across suture plane.*—3 1/16" [77.8 mm.].
*Average diameter across cheek plane.*—2 7/8" [73 mm.].
*Typical weight.*—8.2 ounces [232 grams].
Form: Mostly uniform, globose with slight bulging along the suture.
*Longitudinal section form.*—Round.
*Axial view.*—Round.
Suture: A Dark reddish orange [38. d.rO] line located in a shallow groove that extends from the base just beyond the pistil point, with a slight depression beyond the pistil point.
*Near the base.*—A shallow groove.
*Along the side.*—A shallow trough.
*Near the apex.*—A shallow groove.
Ventral surface: Rounded slightly, lipped stronger on one side.
Lips: Unequal.
Cavity: Flaring, suture showing on both sides, Brilliant yellow [83. brill.Y] stem markings typical.
*Depth.*—1/2" [12.7 mm.].
*Breadth.*—1" [25.4 mm.].
Base: Truncate, very slightly cordate if viewed parallel to the suture.
Apex: Rounded with a slight mammiform protrusion.
Pistil point: Apical, 1/16" [1.6 mm.] in length, Dark reddish brown [44. d.rBr] at the tip.
Stem: Medium.
*Average length.*—1/2" [12.7 mm.].
*Average width.*—3/16" [4.8 mm.].
Skin:
*Thickness.*—Medium.
*Surface.*—Pubescent.
*Tenacity.*—Tenacious to flesh.
*Astringency.*—Non-astringent.
*Tendency to crack.*—None observed.
*Color.*—A Deep red [13. Deep R] over a Moderate orange yellow [71. m.OY] background.
*Down.*—Short, does not roll up when rubbed.
Flesh:
*Color.*—Vivid yellow [82. v.Y] with Dark red [16. d.R] bleeding and Dark red [16. d.R] fibers toward the stone.
*Amygdalin.*—Mild.
*Juice.*—Moderate, rich.
*Texture.*—Firm, crisp.
*Ripens.*—Fairly evenly.
*Flavor.*—Moderate acidic, sweet, typically 15-16 brix.
*Aroma.*—Very slight.
*Eating quality.*—Good.

STONE

Type: Freestone.
Form: Oval.
Hilum: Narrow.
Base: Rounded to truncate.
Apex: Rounded with a 1/16" [1.6 mm.] tip.
Sides: Slightly unequal.
Surface: Irregularly furrowed toward the apex, pitted toward the base.
Ridges: Jagged.
External color: Moderate brown [58. m.Br].
Pit wall color when cracked: Light brown [57. l.Br].
Cavity surface color: Deep yellowish brown [75. deep yBr].
Average pit wall thickness: 1/4" [6.4 mm.].
Average length: 1 5/8" [41.3 mm.].
Average width: 1 1/8" [28.6 mm.].
Average breadth: 7/8" [22.2 mm.].
Tendency to split: None observed.
Kernel:
*Form.*—Oval.
*Skin color.*—Brilliant yellow [83. brill.Y].

*Pellicle color*.—Dark brown [59. d.Br].
*Vein color*.—Vivid yellow [82. v.Y].
*Taste*.—Bitter.
*Viable*.—Yes.
*Average width*.—13/16" [20.6 mm.].
*Average length*.—9/16" [14.3 mm.].
*Amygdalin*.—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Red Princess' peach (U.S. Plant Pat. No. 24,729) by having large blossoms, by being self-fertile, and by producing peaches that are mostly red in skin color, yellow in flesh color, fairly globose in shape, acidic in flavor, and firm in texture, but is distinguished therefrom by requiring less chilling hours, and by producing fruit that is freestone instead of clingstone in type, that is somewhat smaller in size, that has a bitter instead of sweet kernel, and that ripens about eighteen days later.

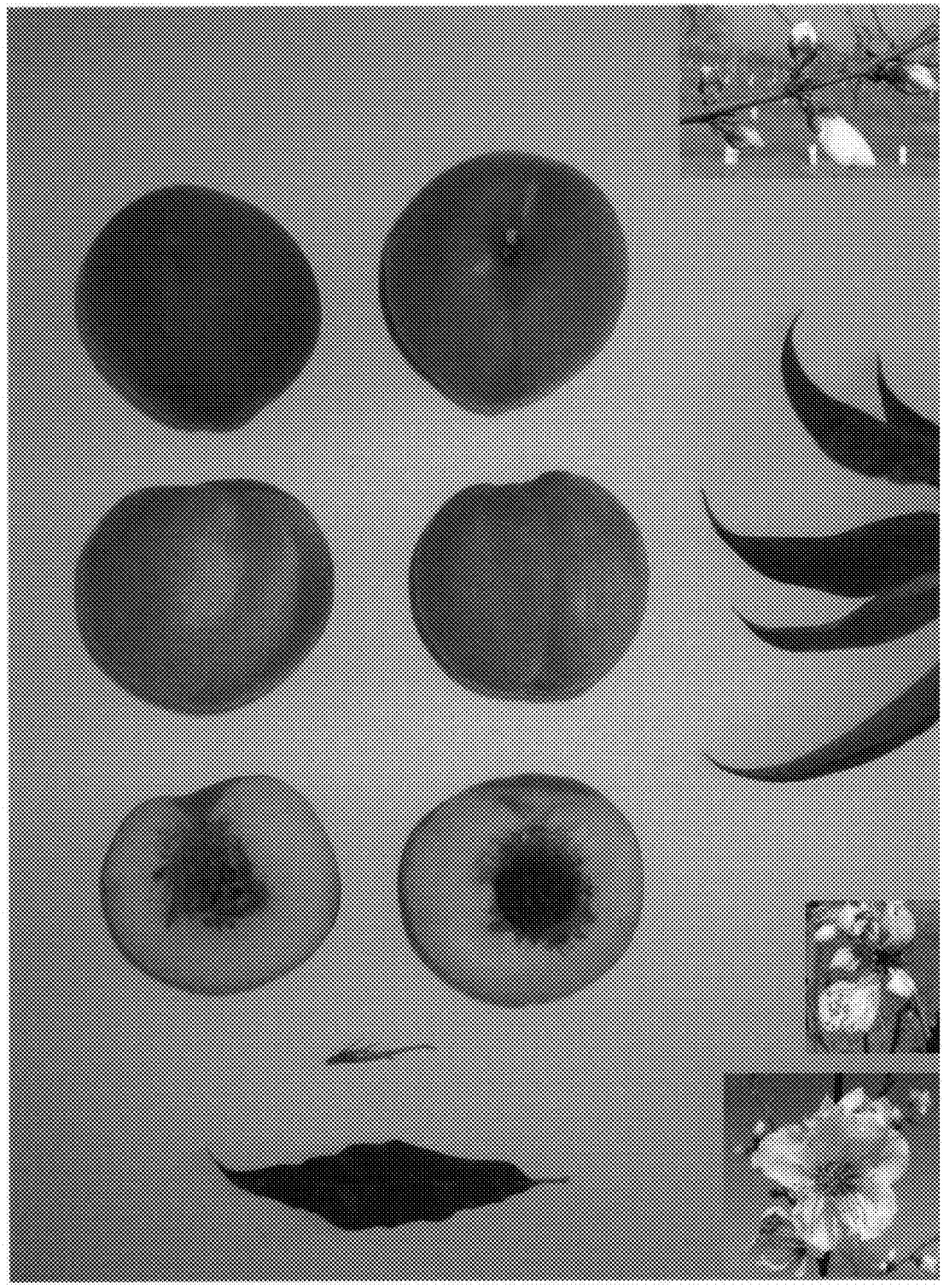

* * * * *